United States Patent
Daniel et al.

(12)

(10) Patent No.: US 6,432,296 B1
(45) Date of Patent: Aug. 13, 2002

(54) POLYMERIC COMPOSITIONS FOR ION-SELECTIVE ELECTRODES

(76) Inventors: Daniel S. Daniel, 3051 St. Paul Blvd., Rochester, NY (US) 14617; Richard L. Detwiler, 422 Woodland La., Webster, NY (US) 14580; Andrew M. Kirsch, 441 N. Burley Rd., Rochester, NY (US) 14612; James E. Love, Jr., 27 Pond Valley Cir., Penfield, NY (US) 14526; Richard C. Sutton, 24 Twilight Dr., Rochester, NY (US) 14617

( * ) Notice: Subject to any disclaimer, the term of this patent is extended or adjusted under 35 U.S.C. 154(b) by 105 days.

(21) Appl. No.: 09/651,048

(22) Filed: Aug. 30, 2000

Related U.S. Application Data

(60) Provisional application No. 60/156,038, filed on Sep. 24, 1999.

(51) Int. Cl.[7] ................................................. G01N 27/31
(52) U.S. Cl. ................. 205/789; 205/778.5; 205/781.5; 205/789.5; 205/793; 204/414; 204/415; 204/418; 204/435
(58) Field of Search .................................. 204/414, 416, 204/418, 421, 435, 415; 205/778.5, 781.5, 787.5, 789, 789.5, 793, 779

(56) References Cited

U.S. PATENT DOCUMENTS

| | | | |
|---|---|---|---|
| 4,199,412 A | | 4/1980 | Battaglia et al. |
| 4,207,109 A | | 6/1980 | Campbell et al. |
| 4,214,968 A | | 7/1980 | Battaglia et al. |
| 4,263,343 A | * | 4/1981 | Kim ............................ 148/266 |
| 4,282,079 A | * | 8/1981 | Chang et al. ................ 204/420 |
| 4,283,504 A | | 8/1981 | Campbell et al. |
| 4,454,007 A | * | 6/1984 | Pace ...................... 204/403.06 |
| 4,476,007 A | | 10/1984 | Battaglia et al. |
| 4,505,800 A | | 3/1985 | Toner et al. |
| 4,980,043 A | * | 12/1990 | Tomita et al. ............... 204/414 |
| 5,032,363 A | * | 7/1991 | Simon et al. ................ 204/416 |
| 6,015,480 A | * | 1/2000 | Craig et al. ................. 204/418 |

OTHER PUBLICATIONS

Cosofret, V.V., "Polymeric Materials for Planar Microfabricated Sensor Technology", Solid State Chemical and Biochemical Sensors, 26, pp. 477–495, 1999.*

* cited by examiner

*Primary Examiner*—Robert J. Warden, Sr.
*Assistant Examiner*—Kaj K. Olsen
(74) *Attorney, Agent, or Firm*—Todd Volyn; James Harrington

(57) ABSTRACT

Improved dry-operative ion-selective electrodes and their use are described. The dry-operative ion-selective electrodes include an internal reference electrode comprising a water-soluble salt dispersed in a polymer binder consisting essentially of a monomer having at least one carboxyl group and a hydrophobic monomer. The polymer provides reduced brittleness, good interlayer adhesion and high salt tolerance.

62 Claims, No Drawings

POLYMERIC COMPOSITIONS FOR ION-SELECTIVE ELECTRODES

This application claims benefit from Provisional application Ser. No. 60/156,038, filed Sep. 24, 1999.

FIELD OF THE INVENTION

The present invention is broadly directed to ion-selective electrodes (ISE's). More specifically, it relates to polymeric compositions for internal reference electrodes of dry-operative ISE's.

BACKGROUND OF THE INVENTION

A wide variety of ion-selective electrodes are known for measuring the amount of an ion in solution. Typically devices for obtaining such measurements include a reference or standard electrode and a separate ion-selective electrode. When simultaneously contacting a solution to be analyzed, the reference or standard electrode and the ion-selective electrode together constitute an electrochemical cell across which a potential difference develops in proportion to the logarithm of the activity of the ion to which the ion-selective electrode is sensitive. The activity is related to the concentration of the ion in the solution. The relationship between potential difference and ion activity in solution is described by the well-known Nernst equation. An electrometric device, usually either a direct reading circuit or a null-balance potentiometric circuit, is employed for measuring the potential between the electrodes.

In principle, an ion-selective electrode can be constructed which is sensitive to any cationic or anionic substance. Cations that can be determined include, but are not limited to, group IA ions, such as sodium, potassium, lithium (alkali metals) and hydrogen; group IIA metal ions such as calcium and magnesium (alkaline earths); metal ions from groups VIA, VIIA, VIIIA, IB, IIB and IIIB; and lead ion from group IVB. Anions include, but are not limited to, halide ions, chloride and fluoride being of particular interest. Carbon dioxide, which is non-ionic, can be determined using an ISE sensitive to hydrogen ion.

Ionic substances are present in a wide range of sample types, including but not limited to, industrial effluents, tap water, rain water, sewer water, biological sources, such as plant and animal derived fluids, and so forth. Human biological fluids are of particular interest and include whole blood, serum, plasma, saliva, sweat, bronchial fluid, vaginal excretions, and so on.

Electrodes based on ion-selective glass membranes are well-known. Solid-state electrodes are also known, such as those described in U.S. Pat. No. 3,856,649 to Genshaw et al. (the '649 patent) and in a paper entitled "Miniature Solid State Potassium Electrode for Serum Analysis" in Analytical Chemistry, v45, pp 1782-84 (1973). An advance in solid-state electrodes has been achieved with the "dry-operative" electrodes described in U.S. Pat. No. 4,214,968 to Battaglia et. al. (the '968 patent), U.S. Pat. No. 4,053,381 to Hamblen et al. and U.S. Pat. No. 4,487,679 to Stare.

Metal, insoluble metal salt solid-state electrodes comprise an electrically conductive inner element, a metal, having disposed thereon an insoluble salt of the metal. The metal, insoluble metal salt combination represents a half-cell or in the context of the present invention, an internal reference electrode, which can be used directly by contacting it with a solution containing an ion to be measured. Alternatively, the internal reference electrode can comprise in intimate contact with the metal and insoluble metal salt, a water-soluble salt dispersed in a hydrophilic "binder" capable of forming a solid matrix. The anion of the water-soluble salt has the same identity as the anion of the insoluble metal salt. In intimate contact with the matrix of the internal reference electrode is a hydrophobic zone which shields the internal reference electrode from direct contact with the ion-containing solution. The hydrophobic zone generally comprises an ion-specific carrier.

The '649 patent describes the use of polyvinyl alcohol as binder to form a hydrophilic layer which includes a water-soluble salt.

The '968 patent lists several binders for the "dried" reference electrolyte solution: polyvinyl alcohol, gelatin, agarose, deionized gelatin, polyacrylamide, polyvinyl pyrrolidone, poly(hydroxyethyl acrylate), poly(hydroxyethyl methacrylate) and poly(acrylic acid). Deionized gelatin is a preferred binder in the '968 patent. Unfortunately, in dry-operative ISE's, the layer comprising the internal reference electrode having gelatin as binder, is brittle, it does not adhere well to the hydrophobic overlayer, and is sensitive to variations in humidity. As a result, the integrity and performance of these ISE's are adversely affected.

SUMMARY OF THE INVENTION

We have found that improved dry-operative ion-selective electrode performance can be achieved using as binder, copolymers prepared from a hydrophilic monomer having at least one carboxylic acid group or salt thereof and a hydrophobic monomer. The resulting copolymer has a glass transition temperature lower than the acid homopolymer, provides good interlayer adhesion as well as high salt tolerance.

In one aspect the present invention relates to dry-operative ion-selective electrodes comprising:

a) an internal reference electrode comprising a water-soluble salt dispersed in a polymer consisting essentially of 60 to 99 weight percent of a monomer having at least one carboxyl group or salt thereof and 1 to 40 weight percent of a hydrophobic monomer; and b) a hydrophobic zone in contact with the internal reference electrode, said hydrophobic zone having distributed therein a carrier selective for the ion.

The internal reference electrode can be a metal salt, insoluble metal salt type electrode, or an oxidation-reduction type electrode comprising a metal and a redox salt couple. The dry-operative ion-selective electrode may further comprise a support wherein the internal reference electrode is disposed between the support and the hydrophobic zone. In preferred embodiments, the binder polymer comprises 70 to 95 weight percent of a monomer having at least one carboxyl group or salt thereof and 5 to 30 weight percent of a hydrophobic monomer.

Preferred polymers of the invention consist essentially of a monomer of formula

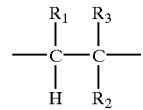

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

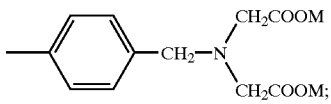

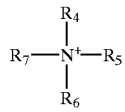

wherein $R_4$, R5, $R_6$, $R_7$ are independently H, methyl, or ethyl, and a monomer of formula

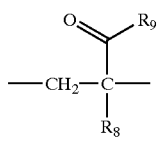

wherein $R_8$ is H or methyl; $R_9$ is methoxy, ethoxy, propoxy, butoxy, hexoxy or —$NHCH_3$.

In another aspect the present invention relates to a method for determining the presence or amount of an ion in a liquid comprising:

A) contacting a dry-operative ion-selective first electrode with a sample of the liquid wherein the dry-operative first electrode comprises
 a) an internal reference electrode comprising a water-soluble salt dispersed in a polymer consisting essentially of 60 to 99 weight percent of a monomer having at least one carboxyl group or salt thereof and 1 to 40 weight percent of a hydrophobic monomer; and
 b) a hydrophobic zone in contact with the internal reference electrode, said hydrophobic zone having distributed therein a carrier selective for the ion, B) contacting a second electrode with a solution comprising a known or constant amount of an ion to which said second electrode is selective, and wherein said dry-operative first electrode and said second electrode are in electrochemical contact or are capable of being in electrochemical contact; or C) contacting the dry-operative ion-selective first electrode and the second electrode with the same sample of the liquid wherein the sample comprises a known or constant amount of an ion to which said second electrode is selective; and D) measuring the potential difference between the dry-operative first electrode and the second electrode as a determination of the presence or amount of the ion in the liquid sample.

The second electrode in the above method of determining an ion can be any suitable reference electrode, such as a calomel electrode or others known in the art, or a solid-state electrode, such as a dry-operative electrode. It can be identical in structure and composition to the dry-operative ion-selective first electrode. If the first and second electrodes are selective for the same type of ion then the solution of part B comprises a known or constant amount of said ion. If the second electrode is selective for a second ion type that is different from that to which the first electrode is selective, then the solution comprises the second ion type in a known or constant amount. If the method for determining the presence or amount of an ion is conducted as in part C, then the sample comprises a known or constant amount of a second ion to which the second electrode is selective and which is different from the ion to which the first electrode is selective.

DETAILED DESCRIPTION OF THE INVENTION

As ISE technology is well-known and described in numerous publications, only a brief account of the construction and use of dry-operative electrodes will be provided. Specific details can be found, for instance, in U.S. Pat. Nos. 4,214,968, 4,053,381 and 4,487,679. The invention is illustrated by reference to a preferred embodiment, a metal, insoluble metal salt type electrode. However, the invention is not limited to this type of electrode.

The internal reference electrode can comprise any metal that is commonly used for this purpose; preferably one that readily forms an insoluble salt and has good electrical properties. Such metals include silver, copper, lead, amalgams and the like. The insoluble salt is disposed on a surface portion of the metal and has, as cation, the cation form of the metal. The anion of the insoluble salt is generally a halide or a sulfide. The insoluble salt may be formed by anodizing the metal in a suitable solution, by a physical application of a dispersion of the salt in a suitable carrier that will adhere to the metal or by other suitable methods. The salt may be formed about an end portion of the metal or its position may be varied according to the desired structural features of the electrode. The water-soluble salt is in intimate contact with the metal and insoluble metal salt. It generally has as cation, an alkali or alkaline earth metal, such as sodium, potassium, magnesium, calcium, and barium; and as anion, a halide. Representative salts include but are not limited to NaCl, KCl, KBr, $MgCl_2$, and $BaCl_2$. The water-soluble salt is dispersed in a solid-forming hydrophilic binder, as discussed above. In contact with the binder is a hydrophobic zone. The hydrophobic zone can be formed from any suitable hydrophobic polymeric material such as polyvinyl chloride (PVC), polyvinyl acetate, polymethylmethacrylate, polyvinylidene chloride, polystyrene and the like. An ion-selective carrier dispersed in the hydrophobic zone renders the electrode specific for an ion of choice. A large number of carriers selective for specific ions are known, including but not limited to: valinomycin, which is selective for potassium; cyclic polyethers of various constitution which make the electrode selective for lithium, rubidium, potassium, cesium or sodium ions; tetralactones; biscyclic ethers; cryptands; hemispherands; calixarenes; cyclic amides; macrolide actins (monactin, nonactin, dinactin, trinactin), the enniatin group (enniatin A,B), cyclohexadepsipeptides, gramicidine, nigericin, dianemycin, nystatin, monensin, esters of monensin (especially methyl monensin for sodium ion), antamanide, and alamethicin (cyclic polypeptides); magnesium or zinc uranyl acetate; 6,8-dichlorobenzoylene urea; didecylphosphoric acid-dioctyl phenylphosphonate; tetraphenylboron; tridodecylhexadecylammonium nitrate; and 4-amino-4'-chlorodiphenylhydrochloride barium salt. Other useful carriers are described by Amman et al. in Helv. Chim. Acta, v58, p535 (1975). Useful calcium ion selective electrodes can be prepared using antibiotic A-23187 as the ion carrier and tris(2-ethyl hexyl) phosphate, tri(m-tolyl) phosphate, or dioctyl phenyl phosphonate as the carrier solvent. (See Pressman, B. C., Annual Review of Biochemistry, E. B. Snell, ed., V5, 1976, pp. 501–503). Thus, electrodes can be prepared which are selective for potassium ion, sodium ion, lithium ion, magnesium ion, calcium ion, ammonium ion, hydrogen ion, cesium ion, bromide ion, chloride ion, fluoride ion, or iodide ion, carbonate ion, salicylate ion, nitrate ion, and so forth.

In preferred embodiments the ion-selective electrodes of the invention are multilayered and include a support which may be comprised of any suitable material, such as ceramic, wood, glass, metal, paper or cast, extruded or molded plastic or polymeric materials, and so on.

The presence or amount of an ion in a solution can be determined by measuring the difference in electrical potential (potential difference) between solution 1 and solution 2 (both usually aqueous) in a cell arrangement schematically represented by the following:

electrode 1/solution 1//solution 2/electrode 2

The activity or concentration of the ion of interest in solution 2 (in this case, the solution of unknown concentration) can be derived from the measured potential difference through use of the well-known Nernst equation. Alternatively, any algorithm or method relating the measured potential difference to the amount or effective amount of the ion can be used. Electrode 2 can be a dry-operative ion-selective electrode of the present invention. Electrode 1 can be any suitable reference electrode or standard electrode such as a saturated calomel electrode. It can be a dry-operative ISE of the present invention. Solution 1 can comprise a known amount of the ion whose activity or amount is unknown in solution 2.

The activity or amount of an ion can also can also be determined by measuring the potential difference between two electrodes contacting a single solution containing the ion using a so-called junctionless arrangement represented by the following:

electrode 1/solution/electrode 2 wherein electrode 1 is an ion-selective electrode specific for an ion in the solution. Electrode 2 can be a reference electrode or an ion-selective electrode specific for a different ionic species which is present at a known or constant level in the solution.

EXAMPLES

The polymeric binders of the present invention can be prepared from hydrophilic vinyl addition carboxylic acid monomers or salts thereof including: acrylic acid, methacrylic acid, alpha methyl maleic acid, maleic acid, chlorofumaric acid, fumaric acid, N-(metavinylbenzyl) iminodiacetic acid, N-(paravinylbenzyl)iminodiacetic acid, alpha-chloroacrylic acid, mono-methyl fumarate, 3-acrylamido-3-methylbutanoic acid, and alpha-methylene glutaric acid, and hydrophobic monomers such as, methyl acrylic acid, ethyl acrylic acid, butyl acrylate, propyl acrylate, hexyl acrylate and their methacrylate homologs plus hetero alkyl acrylate and methacrylamides.

Preferred copolymers of the present invention include the carboxylic acid monomers in an amount ranging from 60 to 99 percent by weight, more preferably about 70 to 95 percent by weight. The hydrophobic monomers are present in an amount ranging from 1 to 40, and more preferably 5 to 30 percent by weight. The monomers may or may not be crosslinkable as described in U.S. Pat. No. 4,283,504. The binder polymers of the invention are soluble in aqueous solution wherein the pH is greater than or equal to about pH 5.0, and are insoluble or poorly soluble in organic solvents such as 2-butanone and tetrahydrofuran. organic solvents are used to dissolve the hydrophobic polymers comprising the hydrophobic zone of the ISE. For multilayer ISE's the polymers should be capable of maintaining their structural integrity as an intact layer when over-coated with a hydrophobic polymer coated from an organic solvent.

The polymers of the present invention can be made using well-known polymerization techniques, such as a solution or dope polymerization method in the presence of a suitable catalyst. After the reaction has proceeded for a desired time, the product may be precipitated by pouring the reaction mass into water, washing the precipitate and redissolving it in water containing a suitable hydroxide salt. Emulsion polymerization or other methods, known to those skilled in the art, may also be used. A particular relative amount of carboxylic acid monomer to hydrophobic monomer in the polymer can be obtained by using that particular relative amount of the vinyl addition monomers at the start of the polymerization. The preparation and use of copolymers of acrylic acid and alkyl acrylates for photographic systems are described in U.S. Pat. Nos. 3,062,674 and 3,220,844 both to Houck et al.

The following example illustrates the preparation of a preferred polymer, poly(ethyl acrylic acid-co-acrylic acid (weight ratio 10/90), hereinafter, Polymer A.

Example 1

Preparation of Polymer A

To a five liter round bottom flask equipped with a stirrer (air-driven teflon paddle on a glass shaft), argon gas inlet, and a condenser, was added 3.6 kg deionized, distilled water which was brought to 70° C. and sparged with argon gas for 10 min. To this aqueous solution was added, with continual stirring, 360 g of acrylic acid and 40g of ethyl acrylic acid. After 10 min, 4.0 g of ammonium persulfate dissolved in 10 mL water was added to the mixture. The reaction was maintained at 70° C. under argon for 15 hrs. The solids content was 10.6% (weight/weight, w/w). The solution was cooled to room temperature and the pH adjusted to 6.3 with aqueous sodium hydroxide. The resultant solids content was 11.58% (w/w). Subsequent batches had inherent viscosities in the range 2–3 but viscosities as low as 0.15 measured at 25° C. in 1 N sodium chloride are acceptable.

Dry-Operative Multilayer Sodium and Potassium Ion-Selective Electrodes

Dry-operative slide-format multilayer ion-selective electrodes for the determination of potassium and sodium were prepared to illustrate the present invention. The invention is not limited to slide-format multilayer ISE's, but can be used with other dry-operative electrode configurations, such as bulb-type or capillary-flow type electrodes. Nor is it intended to limit the invention to electrodes selective only for potassium or sodium ions.

Comparative dry-operative multilayer ion-selective electrodes comprising either gelatin or polymer A as binder were prepared essentially as described in U.S. Pat. Nos. 4,053,381 and 4,214,968. The ion-selective carrier for potassium was valinomycin and the carrier for sodium was methyl monensin.

A schematic diagram of a dry-operative multilayer ISE as employed in the examples is shown below:

| |
|---|
| poly(vinyl chloride-co-vinyl acetate) (90/10) hydrophobic polymer overcoat and ion-selective carrier |
| sodium or potassium chloride in gelatin or Polymer A |
| silver chloride |
| silver |
| /////polyethyleneteraphthalate support////// |

The segmented lines are used to signify that metallic silver, silver chloride and water-soluble sodium or potassium salt and binder are combined in intimate contact with each other, although generally not coated simultaneously. The hydrophobic layer is in intimate contact with the layer comprising the reference electrode, but no substantial mixing of the layers occurs, which is symbolized by the continuous line separating the two layers.

Example 2
ISE Keeping

Significant improvements in keeping stability of dry-operative ion-selective electrodes under variable environmental conditions were achieved using the copolymers of the invention as binder.

Table 1 shows the potassium concentrations determined using prepared aqueous solutions of known potassium concentration containing 70 mg/mL bovine serum albumin. Each data point represents the mean of three replicate measurements using electrodes prepared with either gelatin or polymer A as binder, maintained at 15% relative humidity (RH) and 70° F. and compared with identically prepared control ISE's, maintained at 33% RH in a freezer.

TABLE 1

| Potassium Concentration | Bias (mM) Polymer A | | | Bias (mM) Gelatin | | |
|---|---|---|---|---|---|---|
| (mM) | 1 Wk | 2 Wk | 4 Wk | 1 Wk | 2 Wk | 4 Wk |
| 2.0 | −.005 | .001 | .001 | NA | NA | −.01 |
| 3.8 | .001 | −.001 | .002 | −.012 | −.015 | −.020 |
| 5.3 | −.006 | −.005 | −.004 | −.017 | −.018 | −.021 |
| 6.0 | .010 | .008 | .006 | .032 | .038 | .041 |
| 9.2 | .011 | .008 | .005 | .056 | .058 | .060 |

NA = Not Available

After one week at 15% RH there is a significant change in performance of the potassium ISE prepared with gelatin as binder. With polymer A as binder, the estimated concentrations of potassium do not differ significantly from that of the fresh ISE at 33% RH even after 4 weeks at 15% RH.

Example 3
First Slide Bias

First-slide bias is a storage-related effect wherein the first ISE slide element selected from a cartridge container yields a significantly different measurement of ion activity or concentration compared with the remaining ISE slide elements from the same container.

Table 2 displays the first-slide bias observed, using potassium ISE's prepared with either gelatin or polymer A, that were stored in their containers for three days at three different relative humidities at 70° F. Using a single level of potassium in aqueous bovine serum albumin, the bias was calculated by subtracting the mean of 2 to 10 replicate measurements obtained using slides 2 through 9 in a cartridge from the first slide of a cartridge.

TABLE 2

| Percent Relative Humidity | Bias (mM) Polymer A | Bias (mM) Gelatin |
|---|---|---|
| 15 | .04 | .05 |
| 33 | .08 | .07 |
| 50 | .12 | .26 |

The first-slide bias observed at 50% RH is reduced significantly with polymer A as binder compared with gelatin as binder in the prior art electrode.

Example 4
On Analyzer Stability

Table 3 shows the departure from concentrations of sodium obtained using electrodes kept on analyzer compared with electrodes kept in a freezer (freezer control). The electrodes were conditioned, that is, maintained at 22 ° C. at 33% relative humidity, for 7 days prior to packaging.

TABLE 3

| Sodium Concentration | Bias (mM) polymer A | | | Bias (mM) Gelatin | | |
|---|---|---|---|---|---|---|
| (mM) | 1 Wk | 2 Wk | 4 Wk | 1 Wk | 2 Wk | 4 Wk |
| 95 | −0.45 | −0.50 | −0.60 | −0.10 | −0.10 | −2.00 |
| 145 | −0.45 | −0.45 | −0.50 | −0.10 | 0.10 | −3.30 |
| 195 | −0.35 | −0.55 | −0.65 | 1.30 | 1.60 | −3.70 |

Table 4 shows the change in the percent coefficient of variation (%CV) calculated from the data in Table 3.

TABLE 4

| Concentration | Percent CV Polymer A | | | Percent CV Standard Formula | | |
|---|---|---|---|---|---|---|
| (mM) | 1 Wk | 2 Wk | 4 Wk | 1 Wk | 2 Wk | 4 Wk |
| 95 | .39 | .45 | .54 | .46 | .51 | 1.38 |
| 145 | .26 | .22 | .39 | .58 | .67 | .92 |
| 195 | .32 | .29 | .44 | .65 | .46 | 1.7 |

Tables 5 and 6 show similar results for identical sodium electrodes prepared with polymer A as binder except the electrodes were not preconditioned prior to packaging.

TABLE 5

| Concentration | Bias from Freezer Control (mM) | | |
|---|---|---|---|
| (mM) | 1 Wk | 2 Wk | 4 Wk |
| 95 | −.50 | −.20 | −.60 |
| 145 | −.90 | −.70 | −1.05 |
| 195 | −.30 | .50 | −.50 |

TABLE 6

| Concentration | Percent CV | | |
|---|---|---|---|
| (mM) | 1 Wk | 2 Wk | 4 Wk |
| 95 | .72 | .55 | .32 |
| 145 | .68 | .57 | .50 |
| 195 | .68 | .31 | .77 |

Sodium ISE's comprising polymer A as binder in the electrolyte layer are significantly more robust under environmental variations compared with prior art sodium ISE's prepared with gelatin as binder.

In general, the polymeric compositions of the present invention, when used as binder for the internal reference electrode in dry-operative ISE's provide the following advantages: reduced brittleness, improved adherence to the hydrophobic overcoat, less susceptibility to variations in ambient humidity, compatibility with concentrations of water-soluble salt up to 1 molar, and ISE's having improved performance.

The present invention has been described in detail with respect to particular preferred embodiments. It will be understood that variations and modifications can be effected without departing from the scope and spirit of the invention. The entire contents of all cited patents, patent applications, and non-patent disclosures are expressly incorporated herein by reference.

What is claimed is:

1. A dry-operative ion-selective electrode comprising:
   a) an internal reference electrode comprising a water-soluble salt dispersed in a polymer consisting essentially of 60 to 99 weight percent of a monomer having at least one carboxyl group or salt thereof and 1 to 40 weight percent of a hydrophobic monomer; and
   b) a hydrophobic zone in contact with the internal reference electrode, said hydrophobic zone having distributed therein a carrier selective for the ion.

2. The dry-operative ion-selective electrode of claim 1 further comprising a support, wherein the internal reference electrode is disposed between the support and the hydrophobic zone.

3. The dry-operative ion-selective electrode of claim 1 wherein the polymer consists essentially of 70 to 95 weight percent of a monomer having at least one carboxyl group or salt thereof and 5 to 30 weight percent of a hydrophobic monomer.

4. A dry-operative ion-selective electrode comprising:
   a) an internal reference electrode comprising a water-soluble salt dispersed in a polymer consisting essentially of
      i) 60 to 99 weight percent of a monomer of formula

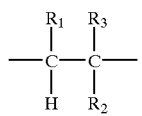

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

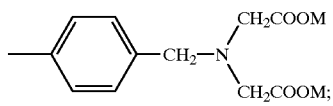

M is H, alkali metal

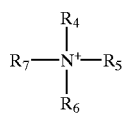

wherein $R_4$, $R_5$, $R_6$, $R_7$ are independently H, methyl, or ethyl, and ii) 1 to 40 weight percent of a monomer of formula

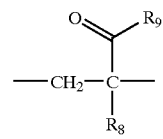

wherein $R_8$ is H or methyl; $R_9$ is methoxy, ethoxy, propoxy, butoxy, hexoxy or —NHCH$_3$; and
   b) a hydrophobic zone in contact with the internal reference electrode, said hydrophobic zone having distributed therein a carrier selective for the ion.

5. The dry-operative ion-selective electrode of claim 4 further comprising a support, wherein the internal reference electrode is disposed between the support and the hydrophobic zone.

6. The dry-operative ion-selective electrode of claim 4 wherein the monomer in (i) is 70 to 95 weight percent and the monomer in (ii) is 5 to 30 weight percent.

7. The dry-operative ion-selective electrode of claim 4 wherein the ion-carrier is selective for cations.

8. The dry-operative ion-selective electrode of claim 4 wherein the ion-carrier is selective for anions.

9. The dry-operative ion-selective electrode of claim 4 wherein the ion-carrier is selective for metal ions.

10. The dry-operative ion-selective electrode of claim 4 wherein the ion-carrier is selective for alakali metal ions or alkaline earth metal ions.

11. The dry-operative ion-selective electrode of claim 4 wherein the ion-carrier is selective for potassium ion, sodium ion, lithium ion, magnesium ion, calcium ion, ammonium ion, hydrogen ion, cesium ion, bromide ion, chloride ion, fluoride ion, iodide ion, carbonate ion, salycilate ion or nitrate ion.

12. The dry-operative ion-selective electrode of claim 4 wherein the polymer is poly(ethyl acrylic acid-co-acrylic acid) or a salt thereof.

13. The dry-operative ion-selective electrode of claim 12 wherein ethyl acrylic acid is 10 weight percent and acrylic acid is 90 weight percent.

14. The dry-operative ion-selective electrode of claim 4 wherein said ion carrier is selected from the group consisting of valinomycin, a cyclic polyether, biscyclic ethers, cryptands, hemispherands, calixarenes, cyclic amides, tetraphenyl borate, a tetralactone, a macrolide acetone, a cyclic polypeptide, a quarternary ammonium salt, monensin, and esters of monensin.

15. A dry-operative ion-selective electrode comprising:
   a) an internal reference electrode comprising a metal, an insoluble metal salt, a water-soluble salt, said water-soluble salt being dispersed in a polymer consisting essentially of 60 to 99 weight percent of a monomer having at least one carboxyl group or salt thereof and 1 to 40 weight percent of a hydrophobic monomer; and
   b) a hydrophobic zone in contact with the internal reference electrode, said hydrophobic zone having distributed therein a carrier selective for the ion.

16. The dry-operative ion-selective electrode of claim 15 further comprising a support, wherein the internal reference electrode is disposed between the support and the hydrophobic zone.

17. The dry-operative ion-selective electrode of claim 15 wherein the polymer consists essentially of 70 to 95 weight percent of a monomer having at least one carboxyl group or salt thereof and 5 to 30 weight percent of a hydrophobic monomer.

18. A dry-operative ion-selective electrode comprising:
a) an internal reference electrode comprising a metal, an insoluble metal salt, a water-soluble salt, said water-soluble salt being dispersed in a polymer consisting essentially of
i) 60 to 99 weight percent of a monomer of formula

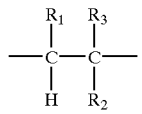

wherein $R_1$ is H or —COOM; $R_2$ is H, Cl or —COOM; $R_3$ is —COOM, —CH$_2$CH$_2$COOM, —CHCONHC (CH$_3$) $_2$CH$_2$COOM, or

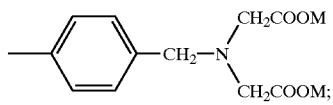

M is H, alkali metal

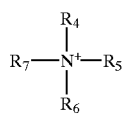

wherein $R_4$, R5, R6, $R_7$ are independently H, methyl, or ethyl, and
ii) 1 to 40 weight percent of a monomer of formula

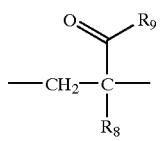

wherein $R_8$ is H or methyl; $R_9$ is methoxy, ethoxy, propoxy, butoxy, hexoxy or NHCH$_3$; and
b) a hydrophobic zone in contact with the internal reference electrode, said hydrophobic zone having distributed therein a carrier selective for the ion.

19. The dry-operative ion-selective electrode of claim 18 further comprising a support, wherein the internal reference electrode is disposed between the support and the hydrophobic zone.

20. The dry-operative ion-selective electrode of claim 18 wherein the monomer in (i) is 70 to 95 weight percent and the monomer in (ii) is 5 to 30 weight percent.

21. The dry-operative ion-selective electrode of claim 18 wherein the ion-carrier is selective for cations.

22. The dry-operative ion-selective electrode of claim 18 wherein the ion-carrier is selective for anions.

23. The dry-operative ion-selective electrode of claim 18 wherein the ion-carrier is selective for metal ions.

24. The dry-operative ion-selective electrode of claim 18 wherein the ion-carrier is selective for alakali metal ions or alkaline earth metal ions.

25. The dry-operative ion-selective electrode of claim 18 wherein the ion-carrier is selective for potassium ion, sodium ion, lithium ion, magnesium ion, calcium ion, ammonium ion, hydrogen ion, cesium ion, bromide ion, chloride ion, fluoride ion, iodide ion, carbonate ion, salycilate ion or nitrate ion.

26. The dry-operative ion-selective electrode of claim 18 wherein the polymer is poly(ethyl acrylic acid-co-acrylic acid) or a salt thereof.

27. The dry-operative ion-selective electrode of claim 26 wherein ethyl acrylic acid is 10 weight percent and acrylic acid is 90 weight percent.

28. The dry-operative ion-selective electrode of claim 18 wherein said ion carrier is selected from the group consisting of valinomycin, a cyclic polyether, biscyclic ethers, cryptands, hemispherands, calixarenes, cyclic amides, tetraphenyl borate, a tetralactone, a macrolide acetone, a cyclic polypeptide, a quarternary ammonium salt, monensin, and esters of monensin.

29. A method for determining the presence or amount of an ion in a liquid comprising:
A) contacting a dry-operative ion-selective first electrode with a sample of the liquid wherein the dry-operative first electrode comprises
a) an internal reference electrode comprising a water-soluble salt dispersed in a polymer consisting essentially of 60 to 99 weight percent of a monomer having at least one carboxyl group or salt thereof and 1 to 40 weight percent of a hydrophobic monomer; and
b) a hydrophobic zone in contact with the internal reference electrode, said hydrophobic zone having distributed therein a carrier selective for the ion,
B) contacting a second electrode with a solution comprising a known or constant amount of an ion to which said second electrode is selective and wherein said dry-operative first electrode and said second electrode are in electrochemical contact or are capable of being in electrochemical contact; or
C) contacting the dry-operative ion-selective first electrode and the second electrode with the same sample of the liquid, wherein the sample comprises a known or constant amount of an ion to which said second electrode is selective; and
D) measuring the potential difference between the dry-operative first electrode and the second electrode as a determination of the presence or amount of the ion in the liquid sample.

30. The method of claim 29 wherein the dry-operative first electrode comprises a support and the internal reference electrode is disposed between the support and the hydrophobic zone, and wherein said first electrode and said second electrode in B are selective for the same ion.

31. The method of claim 29 wherein the polymer consists essentially of 70 to 95 weight percent of a monomer having at least one carboxyl group or salt thereof and 5 to 30 weight percent of a hydrophobic monomer.

32. A method for determining the presence or amount of an ion in a liquid comprising:
A) contacting a dry-operative ion-selective first electrode with a sample of the liquid wherein the dry-operative first electrode comprises
a) an internal reference electrode comprising a water-soluble salt dispersed in a polymer consisting essentially of i) 60 to 99 weight percent of a monomer of formula

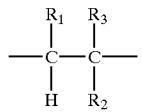

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

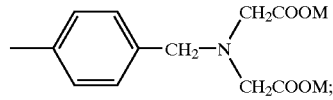

M is H, alkali metal

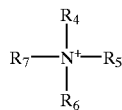

wherein $R_4$, R5, $R_6$, $R_7$ are independently H, methyl, or ethyl, and ii) 1 to 40 weight percent of a monomer of formula

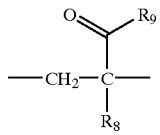

wherein $R_8$ is H or methyl; $R_9$ is methoxy, ethoxy, propoxy, butoxy, hexoxy or —NHCH$_3$, b) a hydrophobic zone, in contact with the internal reference electrode, said hydrophobic zone having distributed therein a carrier selective for the ion;

B) contacting a second electrode with a solution comprising a known or constant amount of an ion to which said second electrode is selective and wherein said dry-operative first electrode and said second electrode are in electrochemical C) contacting the dry-operative ion-selective first electrode and the second electrode with the same sample of the liquid, wherein the sample comprises a known or constant amount of an ion to which said second electrode is selective; and D) measuring the potential difference between the dry-operative first electrode and the second electrode as a determination of the presence or amount of the ion in the liquid sample.

33. The method of claim 32 wherein the dry-operative first electrode comprises a support and the internal reference electrode is disposed between the support and the hydrophobic zone, and wherein said first electrode and said second electrode in B are selective for the same ion.

34. The method of claim 32 wherein the monomer in (i) is 70 to 95 weight percent and the monomer in (ii) is 5 to 30 weight percent.

35. The method of claim 32 wherein the ion-carrier is selective for cations.

36. The method of claim 32 wherein the ion-carrier is selective for anions.

37. The method of claim 32 wherein the ion-carrier is selective for metal ions.

38. The method of claim 32 wherein the ion-carrier is selective for alakali metal ions or alkaline earth metal ions.

39. The method of claim 32 wherein the ion-carrier is selective for potassium ion, sodium ion, lithium ion, magnesium ion, calcium ion, ammonium ion, hydrogen ion, cesium ion, bromide ion, chloride ion, fluoride ion, iodide ion, carbonate ion, salycilate ion or nitrate ion.

40. The method of claim 32 wherein the polymer is poly(ethyl acrylic acid-co-acrylic acid) or a salt thereof.

41. The method of claim 40 wherein ethyl acrylic acid is 10 weight percent and acrylic acid is 90 weight percent.

42. The method of claim 32 wherein the second electrode is a dry-operative electrode.

43. The method of claim 42 wherein the dry-operative second electrode comprises a) an internal reference electrode comprising a water-soluble salt dispersed in a polymer consisting essentially of i) 60 to 99 weight percent of a monomer of formula

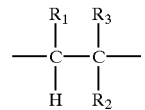

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

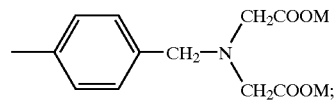

M is H, alkali metal

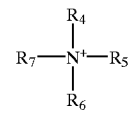

wherein $R_4$, $R_5$, $R_6$, $R_7$ are independently H, methyl, or ethyl, and ii) 1 to 40 weight percent of a monomer of formula

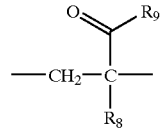

wherein $R_8$ is H or methyl; $R_9$ is methoxy, ethoxy, propoxy, butoxy, hexoxy or —NHCH$_3$; and b) a hydrophobic zone in contact with the internal reference electrode, said hydrophobic zone having distributed therein a carrier selective for the ion.

44. The method of claim 43 wherein the dry-operative first electrode and the dry-operative second electrode have the same structure and composition.

45. The method of claim 32 wherein said ion is carrier is selected from the group consisting of valinomycin, a cyclic polyether, biscyclic ethers, cryptands, hemispherands, calixarenes, cyclic amides, tetraphenyl borate, a tetralactone, a macrolide acetone, a cyclic polypeptide, a quarternary ammonium salt, monensin, and esters of monensin.

46. A method for determining the presence or amount of an ion in a liquid comprising:
A) contacting a dry-operative ion-selective first electrode with a sample of the liquid, wherein said first electrode comprises
  a) an internal reference electrode comprising a metal, an insoluble metal salt, a water-soluble salt, said water-soluble salt being dispersed in a polymer consisting essentially of 60 to 99 having at least one carboxyl group or salt thereof and 1 to 40 weight percent of a hydrophobic monomer; and,
  b) a hydrophobic zone in contact with the internal reference electrode, said hydrophobic zone having distributed therein a carrier selective for the ion;
B) contacting a second electrode with a solution comprising a known or constant amount of an ion to which said second electrode is selective and wherein said dry-operative first electrode and said second electrode are in electrochemical contact or are capable of being in electrochemical contact; or
C) contacting the dry-operative ion-selective first electrode and the second electrode with the same sample of the liquid, wherein the sample comprises a known or constant amount of an ion to which said second electrode is selective; and
D) measuring the potential difference between the dry-operative first electrode and the second electrode as a determination of the presence or amount of the ion in the liquid sample.

47. The method of claim 46 wherein the dry-operative first electrode comprises a support and the internal reference electrode is disposed between the support and the hydrophobic zone, and wherein said first electrode and said second electrode in B are selective for the same ion.

48. The method of claim 46 wherein the polymer consists essentially of 70 to 95 weight percent of a monomer having at least one carboxyl group or salt thereof and 5 to 30 weight percent of a hydrophobic monomer.

49. A method for determining the presence or amount of an ion in a liquid comprising:
A) contacting a dry-operative ion-selective first electrode with a sample of the liquid, wherein said first electrode comprises
  a) an internal reference electrode comprising a metal, an insoluble metal salt, a water-soluble salt, said water-soluble salt being dispersed in a polymer consisting essentially of
    i) 60 to 99 weight percent of a monomer of formula

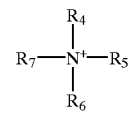

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

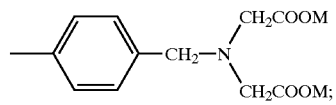

M is H, alkali metal

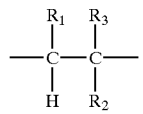

wherein $R_4$, $R_5$, R6, $R_7$ are independently H, methyl, or ethyl, and
    ii) 1 to 40 weight percent of a monomer of formula

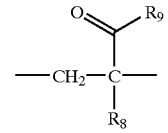

wherein $R_8$ is H or methyl; $R_9$ is methoxy, ethoxy, propoxy, butoxy, hexoxy or —NHCH$_3$,
  b) a hydrophobic zone in contact with the internal reference electrode, said hydrophobic zone having distributed therein a carrier selective for the ion;
B) contacting a second electrode with a solution comprising a known or constant amount of an ion to which said second electrode is selective and wherein said dry-operative first electrode and said second electrode are in electrochemical contact or are capable of being in electrochemical contact; or
C) contacting the dry-operative ion-selective first electrode and the second electrode with the same sample of the liquid, wherein the sample comprises a known or constant amount of an ion to which said second electrode is selective; and
D) measuring the potential difference between the dry-operative first electrode and the second electrode as a determination of the presence or amount of the ion in the liquid sample.

50. The method of claim 49 wherein the dry-operative first electrode comprises a support and the internal reference electrode is disposed between the support and the hydrophobic zone, and wherein said first electrode and said second electrode in B are selective for the same ion.

51. The method of claim 49 wherein the monomer in (i) is 70 to 95 weight percent and the monomer in (ii) is 5 to 30 weight percent.

52. The method of claim 49 wherein the ion-carrier is selective for cations.

53. The method of claim 49 wherein the ion-carrier is selective for anions.

54. The method of claim 49 wherein the ion-carrier is selective for metal ions.

55. The method of claim 49 wherein the ion-carrier is selective for alakali metal ions or alkaline earth metal ions.

56. The method of claim 49 wherein the ion-carrier is selective for potassium ion, sodium ion, lithium ion, magnesium ion, calcium ion, ammonium ion, hydrogen ion, cesium ion, bromide ion, chloride ion, fluoride ion, iodide ion, carbonate ion, salycilate ion or nitrate ion.

57. The method of claim 49 wherein the polymer is poly(ethyl acrylic acid-co-acrylic acid) or salt thereof.

58. The method of claim 57 wherein ethyl acrylic acid is 10 weight percent and acrylic acid is 90 weight percent.

59. The method of claim 49 wherein the second electrode is a dry-operative electrode.

60. The method of claim 59 wherein the dry-operative second electrode comprises a) an internal reference electrode comprising a water-soluble salt dispersed in a polymer consisting essentially of i) 60 to 99 weight percent of a monomer of formula

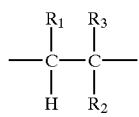

wherein $R_1$ is H or —COOM; $R_2$ is H, Cl or —COOM; $R_3$ is —COOM, —CH$_2$CH$_2$COOM, —CHCONHC(CH$_3$)$_2$CH$_2$COOM, or

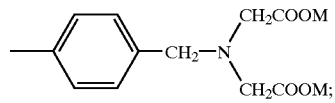

M is H, alkali metal

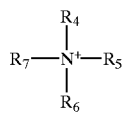

wherein $R_4$, $R_5$, $R_6$, $R_7$ are independently H, methyl, or ethyl, and ii) 1 to 40 weight percent of a monomer of formula

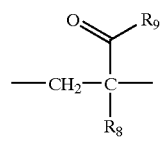

wherein $R_8$ is H or methyl; $R_9$ is methoxy, ethoxy, propoxy, butoxy, hexoxy or —NHCH$_3$; and b) a hydrophobic zone in contact with the internal reference electrode, said hydrophobic zone having distributed therein a carrier selective for the ion.

61. The method of claim 60 wherein the dry-operative first electrode and the dry-operative second electrode have the same structure and composition.

62. The method of claim 49 wherein said ion carrier is selected from the group consisting of valinomycin, a cyclic polyether, biscyclic ethers, cryptands, hemispherands, calixarenes, cyclic amides, tetraphenyl borate, a tetralactone, a macrolide acetone, a cyclic polypeptide, a quarternary ammonium salt, monensin, and esters of monensin.

\* \* \* \* \*

UNITED STATES PATENT AND TRADEMARK OFFICE
CERTIFICATE OF CORRECTION

PATENT NO.   : 6,432,296 B1
DATED        : August 13, 2002
INVENTOR(S)  : Daniel et al.

It is certified that error appears in the above-identified patent and that said Letters Patent is hereby corrected as shown below:

Column 9,
Lines 60-67, should read as follows:

-- cation or 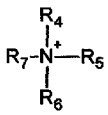 wherein $R_4$, $R_5$, $R_6$, $R_7$ are independently H, methyl, or ethyl, and --

Column 11,
Lines 24-32, should read as follows:

-- cation or 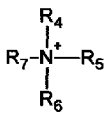 wherein $R_4$, $R_5$, $R_6$, $R_7$ are independently H, methyl, or ethyl, and --

Column 13,
Lines 19-27, should read as follows:

-- cation or 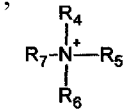 wherein $R_4$, $R_5$, $R_6$, $R_7$ are independently H, methyl, or ethyl, and --

Column 14,
Lines 36-44, should read as follows:

-- cation or 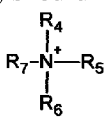 wherein $R_4$, $R_5$, $R_6$, $R_7$ are independently H, methyl, or ethyl, and --

Column 16,
Lines 2-9, should read as follows:

-- cation or 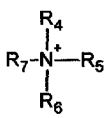 wherein $R_4$, $R_5$, $R_6$, $R_7$ are independently H, methyl, or ethyl, and --

UNITED STATES PATENT AND TRADEMARK OFFICE
CERTIFICATE OF CORRECTION

PATENT NO. : 6,432,296 B1
DATED : August 13, 2002
INVENTOR(S) : Daniel et al.

It is certified that error appears in the above-identified patent and that said Letters Patent is hereby corrected as shown below:

Column 17,
Lines 21-28, should read as follows:

-- cation or $\begin{array}{c} R_4 \\ | \\ R_7-\overset{+}{N}-R_5 \\ | \\ R_6 \end{array}$ wherein $R_4$, $R_5$, $R_6$, $R_7$ are independently H, methyl, or ethyl, and --

Signed and Sealed this

Thirtieth Day of September, 2003

JAMES E. ROGAN
*Director of the United States Patent and Trademark Office*